United States Patent [19]

Saito et al.

[11] 4,086,206
[45] Apr. 25, 1978

[54] ORGANOPHOSPHORUS COMPOUNDS AND PROCESS FOR THE PRODUCTION THEREOF

[75] Inventors: Toranosuke Saito; Masakatu Kitani, both of Kobe; Kenshi Mori, Omuta; Shinichi Izawa, Kawasaki, all of Japan

[73] Assignees: Sanko Kaihatsu Kagaku Kenkyosho, Osaka; Asahi-Dow Limited, Tokyo, both of Japan

[21] Appl. No.: 812,943

[22] Filed: Jul. 5, 1977

[30] Foreign Application Priority Data

Jul. 5, 1976 Japan .................................. 51-78874
Jun. 6, 1977 Japan .................................. 52-65815

[51] Int. Cl.$^2$ .................. C07D 251/18; C07D 251/54; C08K 5/34
[52] U.S. Cl. ................... 260/45.8 NT; 260/45.8 NE; 260/45.8 R; 260/47 XA; 260/880 R; 260/DIG. 24; 544/195; 544/196
[58] Field of Search ............... 260/45.8 NT, 45.8 NE; 544/195; 8/116 P

[56] References Cited

U.S. PATENT DOCUMENTS

| | | | |
|---|---|---|---|
| 3,702,878 | 11/1972 | Saito et al. | 260/936 |
| 3,793,289 | 2/1974 | Koch et al. | 260/45.8 NT |
| 3,876,635 | 4/1975 | Deiner et al. | 260/830 R |
| 3,885,912 | 5/1975 | Golborn et al. | 8/116 P |
| 3,906,136 | 9/1975 | Weil | 8/116 P |

Primary Examiner—Melvyn I. Marquis
Assistant Examiner—R. A. White
Attorney, Agent, or Firm—Sughrue, Rothwell, Mion, Zinn and Macpeak

[57] ABSTRACT

New phosphorus-containing condensation products are obtained by conducting dehydrocondensation of 10-hydroxymethyl-9, 10-dihydro-9-oxa-10-phosphorphenanthrene-10-oxide compounds with melamine or benzoguanamine.

Alternatively, 9,10-dihydro-9-oxa-10-phosphorphenanthrene-10-oxide compounds with alkoxymethyl melamines or alkoxymethyl benzoguanamines are condensed under heating.

These phosphorus-containing condensation products are useful, particularly as a flame retardant for various synthetic resins.

12 Claims, No Drawings

ORGANOPHOSPHORUS COMPOUNDS AND PROCESS FOR THE PRODUCTION THEREOF

BACKGROUND OF THE INVENTION

This invention relates to a new organophosphorus compound and particularly, to phosphorus-containing condensation products and process for the production thereof.

Organophosphorus compounds have been used as a flame retardant for various synthetic resins as disclosed in, for example, U.S. Pat. Nos. 3,247,134, 3,262,894, 3,278,464 and 3,368,916. However, when the conventional organophosphorus compounds are added in an amount sufficient to impart flame retardancy, they have a disadvantage of lowering the thermal deformation or degradation temperature of synthetic resins.

SUMMARY OF THE INVENTION

An object of this invention is to provide new phosphorus-containing condensation products exhibiting a flame-retarding effect on a normally inflammable synthetic resin without lowering the thermal deformation or degradation temperature thereof.

Another object of this invention is to provide a process for the production of phosphorus-containing condensation products.

A further object of this invention is to provide a process for the production of phosphorus-containing condensation products thereby restraining the formation of by-products and advancing a condensation reaction smoothly and safely.

A still further object of this invention is to provide a flame retardant synthetic resin composition containing phosphorus-containing condensation products.

In accordance with this invention, there are provided phosphorus-containing condensation products having the structure of Formula I,

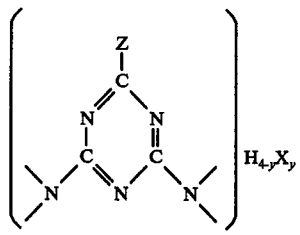

I wherein Z represents

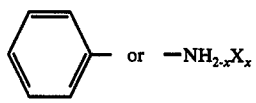

or $-NH_{2-x}X_x$ and X represents radical

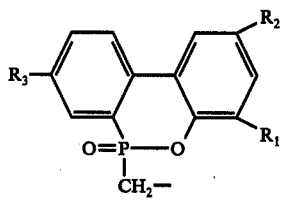

II wherein $R_1$, $R_2$ and $R_3$ each is hydrogen, a halogen atom, an alkyl group of 1 to 8 carbon atoms, an aralkyl group, cyclohexyl or phenyl, $x$ is 0, 1 or 2 and $y$ is from 1 to 4.

In accordance with this invention, there is, also, provided a process for the production of phosphorus-containing condensation products of Formula I, which comprises conducting dehydrocondensation of organophosphorus compounds represented by Formula III,

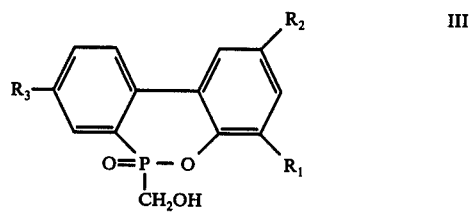

III wherein $R_1$, $R_2$ and $R_3$ are as defined above with melamine or benzoguanamine (Process a).

Alternatively, between organophosphorus compounds represented by Formula IV,

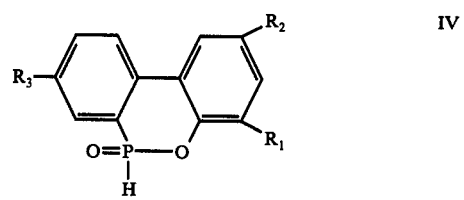

IV wherein $R_1$, $R_2$ and $R_3$ are as defined above and alkoxymethyl melamines or alkoxymethyl benzoguanamines is a heating condensation conducted thereby to obtain phosphorus-containing condensation products of Formula I (Process b).

DETAILED DESCRIPTION OF THE INVENTION

Compounds of Formula III which may be used in this invention are known and may be prepared by effecting an addition reaction of formaldehyde to compounds of Formula IV.

For example, formalin or paraform containing 1.0 − 1.2 mols of formaldehyde is added to 1.0 mol of the compound of Formula IV and reaction is effected at temperatures of 120° − 160° C for about 2 hours. Thereafter the remaining water and formaldehyde are removed from the reaction mixture under a vacuum. Thus compounds of Formula III are obtained with high purity.

Examples of the compound of Formula III include 10-hydroxymethyl-9, 10-dihydro-9-oxa-10-phosphorphenanthrene-10-oxide; 6,8-dichloro-10-hydroxymethyl-9, 10-dihydro-9-oxa-10-phosphorphenan-threne-10-oxide; 2, 6, 8-tri-tert.butyl-10-hydroxymethyl-9, 10-dihydro-9-oxa-10-phosphor-phenanthrene-10-oxide; 2-methyl-6-tert.butyl-8-methyl-10-hydroxymethyl-9, 10-dihydro-9-oxa-10-phosphorphenanthrene-10-oxide; 8-phenyl-10-hydroxymethyl-9, 10-dihydro-9-oxa-10-phosphorphenanthrene-10-oxide; 6, 8-dicyclohexyl-10-hydroxymethyl-9, 10-dihydro-9-oxa-10-phosphor-phenanthrene-10-oxide.

Compounds of Formula IV are known and may be prepared by the method disclosed in U.S. Pat. No. 3,702,878 or Japanese Patent Publication No. 17979/75, or methods similar thereto. For example, compounds of Formula IV′

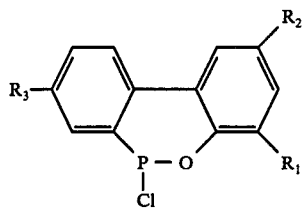

wherein $R_1$, $R_2$ and $R_3$ are as defined above are obtained by reacting 1 mol of a substituted o-phenylphenol compound of Formula IV″

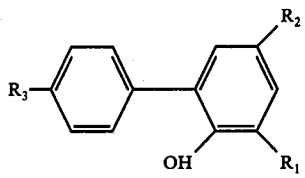

wherein $R_1$, $R_2$ and $R_3$ are as defined above with 1.3 mols of phosphorus trichloride in the presence of 0.003 mols of Zinc chloride at temperatures of 130° to 200° C for about 20 hours. Compounds of Formula IV are thus obtained by adding an excess of water to the compound of Formula IV′ to effect hydrolysis and removing the remaining water under reduced pressure.

Examples of compounds of Formula IV are 9, 10-dihydro-9-oxa-10-phosphorphenanthrene-10-oxide; 6,8-dichloro-9, 10-dihydro-9-oxa-10-phosphorphenanthrene-10-oxide; 6-methyl-9, 10-dihydro-9-oxa-10-phosphorphenanthrene-10-oxide; 2,6,8-tritertiarybutyl-9, 10-dihydro-9-oxa-10-phosphorphenanthrene-10-oxide; 6-phenyl-9, 10-dihydro-9-oxa-10-phosphorphenanthrene-10-oxide; 6,8-dibenzyl-9, 10-dihydro-9-oxa-10-phosphorphenanthrene-10-oxide.

The compound of Formula III alone or in mixture is subject to dehydrocondensation with melamine or benzoguanamine. The dehydrocondensation is almost completed at temperatures of 150° to 250° C during the period of about 2 hours to 10 hours. Although the reaction velocity is accelerated in the presence of a catalyst such as an acid or alkali, the condensation usually advances without catalysts. As the reaction advances, the infrared absorption at wave number 3170 identifying a hydroxyl group of the compound of Formula III disappears or decreases and the infrared absorption at wave number 3390 identifying N-H bonds of melamine or benzoguanamine decreases. This shows that the reaction products have the structure represented by Formulae I or II.

The condensation products of this invention are a colourless or light yellow, transparent, glassy solid, having a softening point of 100° to 180° C. According to liquid chromatography, it is confirmed that the condensation product is composed of a mixture of compounds having different values of $x$ or $y$. Preferebly, $x$ is 0 or 1 and $y$ is from 1 to 2.

According to process b, oxidation products of the compound of Formula IV by-producing during the condensation reaction are reduced below 2% so that the end products of Formula I can be obtained with high purity and thus, enlarged in uses without difficult separation of the by-products.

There is a further advantage that the condensation advances smoothly even at the end of reaction so that the productivity becomes higher. Also, occurrence of combustible gases remarkably decreases and therefore, the danger of fire or explosion can be avoided.

The terms of alkoxymethyl melamines and alkoxymethyl benzoguanamines used herein mean compounds having radical $R_4OCH_2-$ wherein $R_4$ is a lower alkyl group substituted for at least one hydrogen atom of $NH_2$ radical of melamine or benzoguanamine.

The alkoxymethylated melamine and benzoguanamine are known in general as one of amino resins and particularly, used widely in paints.

In view of the chemical structure, melamine may be mono- to hexa- substituted by alkoxymethyl radical and benzoguanamine may be mono- to tetra- substituted by alkoxymethyl radical. However, alkoxymethyl melamines and alkoxymethyl benzoguanamines which are produced in practice have a more complicated composition.

The alkoxymethylated melamine and benzoguanamine which may be used in this invention contain, preferably, free methylol and dimethylene ether radicals in a lesser amount. Melamine mono- to hexa-, preferably di- to tri- substituted by alkoxymethyl and benzoguanamine mono- to tetra-, preferably mono- to di- substituted by alkoxymethyl are suitable. They may, however, contain such radicals as $-NH-CH_2-NH-$ and $-N(CH_2OR_4)_2$ in addition to $-NHCH_2OR_4$, and the condensation of this invention is hardly affected by the presence of such radicals.

This is confirmed by the experimental courses as described hereunder.

The condensation reaction with the compound of Formula IV is mainly a dealcoholization reaction represented by the Experimental formula V,

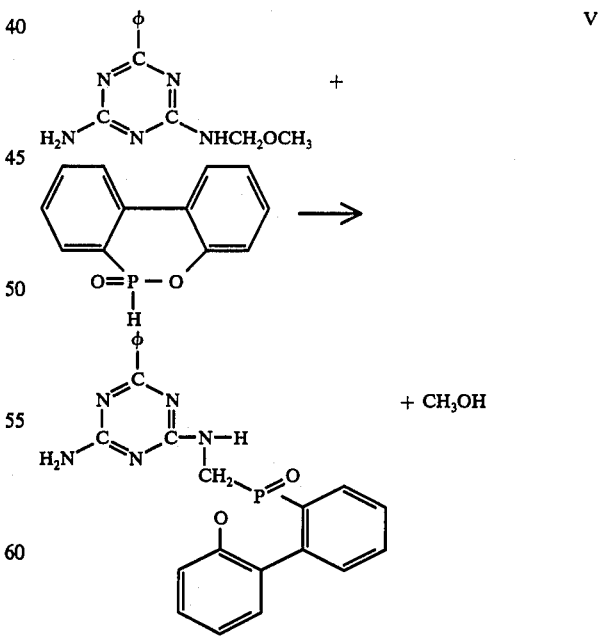

In practice, however, the end products of this invention are produced through a more complicated course of reaction depending on the complicated composition of alkoxymethylated melamine or benzoguanamine.

The foregoing is confirmed by the Experimental formulae VI and VII as set forth hereunder.

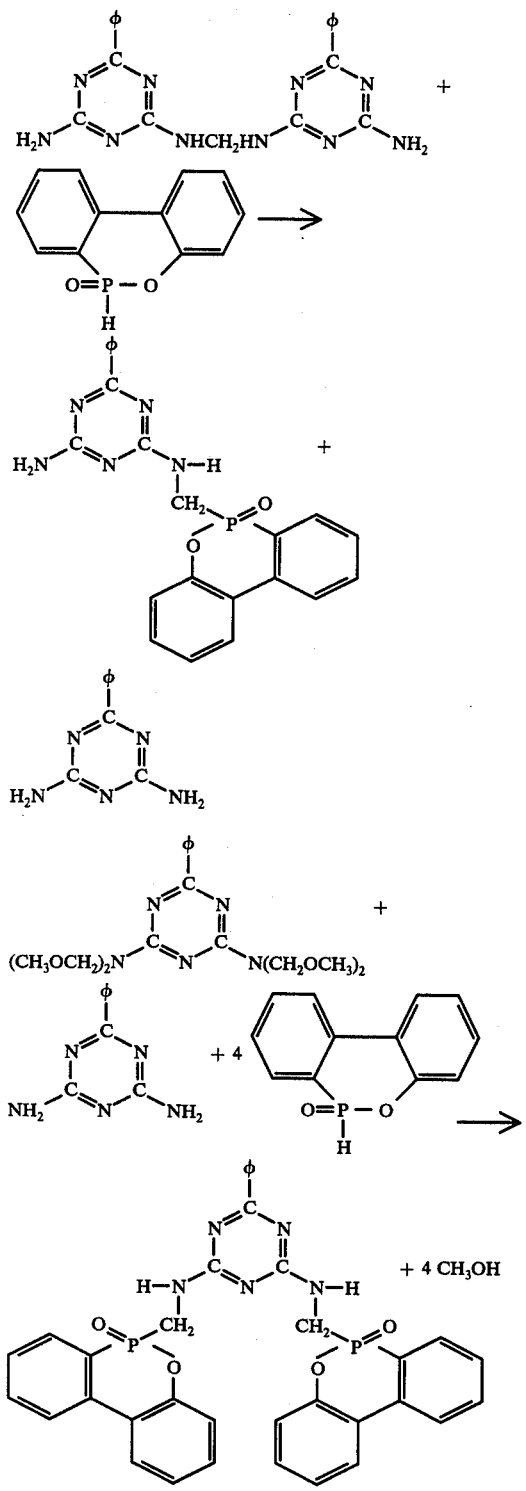

As seen from the structures set forth in the Experimental formulae V, VI and VII, the end products have a strong intramolecular hydrogen bond formed between oxygen of the P=O bond and hydrogen of the N—H bond. Indeed, infrared absorption based on the stretching vibration of the hydrogen-bonded N—H is observed as a broad peak at wave number 3,350.

This shows that the condensation products have the structure of Formula I.

The alkoxymethylated melamine and benzoguanamine which are suitable for this invention may be prepared in the well-known method by methylolating melamine or benzoguanamine with formaldehyde such as formalin or paraform in the presence of an alkaline catalyst and then conducting a dehydrocondensation with alcohols in an acidic condition. Examples of the alcohol which may be used include a lower alcohol such as methanol, ethanol, isopropanol, butanol, sec-butanol or iso-butanol. In order to avoid gelation caused by linkage of triazine rings through methylene radicals, it is preferred to use alcohols in a large excess of the theoretical amount. If the methylolated products of melamine or benzoguanamine are not completely etherified by alcohols, on the occasion of the condensation with the compound of Formula IV water is formed, which is then reacted with the compound of Formula IV at elevated temperatures to form oxidation products.

It is, therefore, preferred that the etherification of the N-methylolated products is effected to completeness either by adding a large amount of alcohol or by shifting the equilibrium while removing the resulting water on the etherification.

In the former manner, alcohols having a small molecular weight; such as methanol are preferred. In the latter manner, alcohols capable of removing water easily by azeotropy, such as butanol, sec-butanol or iso-butanol are preferred. The separation of water from the azeotropic mixture can be more effectively conducted by adding benzene, toluene or xylene.

The alkoxymethylated melamine and benzoguanamine may be reacted with the compound of Formula IV, without removing the catalyst and alcohol involved therein.

Though the condensation is effected under heating, a catalyst may be added to the reaction system, if desired, for shortening the reaction time. The reaction temperature may be elevated up to about 250° C, but it is preferred for preventing reaction products from coloring to maintain the temperature below about 220° C. For the purpose of removing completely volatile materials from the end products, the reaction system may be put under reduced pressure or an inert gas may be blown thereinto.

The reaction time may vary depending on a conversion ratio of reaction, temperature and the presence of a catalyst and its amount, but it is, preferably, within the range of 1 to 10 hours.

As the catalyst, metal compounds which may be effective for a conventional dehydrocondensation may be used. Examples of the catalyst are potassium hydroxide, potassium carbonate, potassium acetate, sodium hydroxide, sodium carbonate, sodium acetate, calcium hydroxide, calcium oxide, barium hydroxide, zinc hydroxide, zinc oxide, zinc acetate, zinc chloride, cadmium chloride, aluminum chloride, germanium oxide, tin chloride and lead acetate, and others.

The course of the condensation may be pursued by liquid chromatography and accordingly, the end of the reaction may be decided.

The condensation product of this invention in the isolated form or as it is may be compounded with a normally inflammable synthetic resin thereby to render it flame retardancy.

Accordingly, this invention, also, provides a flame-retardant resin composition containing compounds of Formula I as a flame-retarding agent.

With amounts of about 2 to 20 parts by weight per 100 parts by weight of resin, a remarkable flame-retardancy is obtained. Examples of the plastics are AS resins, ABS resins, polystyrenes, polycarbonates, polyesters, polyamides, phenoxy resins and others.

On the other hand, when mixed with thermosetting phenolic resins or aminoplasts, the compounds of Formula I participate in a curing reaction to form a part of the cured resin.

With amounts of about 1 to 15 parts by weight per 100 parts by weight of resin, a remarkable flame-retardancy is obtained. Compounds of Formula I may be used in combination with organic halides or metal oxide which are usually used as a flame-retarding agent.

Compounds of this invention may be also used for decolorizing agents, antioxidants, ultraviolet absorbers, coloration preventives and plasticizers in respect of polyolefins, polystyrenes, ABS resins, AS resins, polyacetals, polycarbonates, polyacrylic resins, polysulfones, polyamides, polyesters, epoxy resins, and phenolic resins and others.

Further, compounds of this invention may be used in synthetic fibers such as polyacrylonitrile, polyester and polyamide as a stretch spinning modifier, a dyeing assistance, a light fastness modifier of fibers after dyeing, a heat stabilizer or thermal coloration preventive, a decolorizing agent, a flame retardant material and a flame retardant assistance.

This invention will be illustrated by the following non-limitative examples.

EXAMPLE 1

Preparation of 9, 10-dihydro-9-oxa-10-phosphor-phenanthrene-10-oxide (hereinafter referred to as HCA):

6,800 g of o-phenylphenol and 14 g of zinc chloride are charged into a four-necked flask of 10,000 ml in capacity provided with a stirrer, a thermometer, a dropping funnel and a reflux condenser, and elevated to a temperature of 80° C. 6,500 g of phosphorus trichloride are dropped from the dropping funnel at the same temperature while stirring the contents of the flask.

After completion of the dropping, the temperature is elevated to 180° C and phosphorus trichloride is continuously added to such a degree that reflux of phosphorus trichloride is slowly effected.

When the inside temperature of the flask is lowered by the addition of phosphorus trichloride and no longer elevated, addition of phosphorus trichloride is discontinued and then, heating is effected for 10 hours. The contents are distilled under reduced pressure of 17 mmHg and thus, 10-chloro-9, 10-dihydro-9-oxa-10-phosphorphenanthrene is obtained. When 1,500 g of water are added to this compound at 130° C and after 30 minutes, water is removed under reduced pressure of 10 mmHg, HCA is obtained. Preparation of 10-hydroxymethyl-9, 10-dihydro-9-oxa-10-phosphor-phenanthrene-10-oxide (hereinafter referred to as 10-hydroxymethyl-HCA):

1,517 g (7 mols) of HCA obtained above are charged into a 2,000 ml, four-necked flask provided with a thermometer, a dropping funnel, a water exit and a stirrer, and after elevating to 130° C, stirring is effected. 624 g (1.1 × 7 mols) of a 37% formalin are dropped from the dropping funnel at 150° C. Reaction occurs immediately and water is distilled out. After completion of the dropping, the reaction system is maintained at 160° C for 0.5 hours. Next, the remaining water and formaldehyde are removed at 160° C under reduced pressure of 18 mmHg.

Thus, 1727 g of 10-hydroxymethyl-HCA having the following Formula,

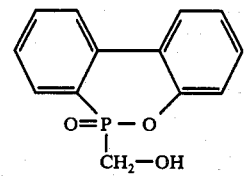

are obtained.

800 g of 10-hydroxymethyl-HCA obtained above and 30 g of melamine are charged into a three-necked, 1000 ml flask provided with a stirrer, a thermometer and a water exit, and elevated to 170° C and then, stirring is effected. After elevating the temperature to 210° C, a dehydration reaction is effected under reduced pressure for 4 hours. The reaction is completed in such a manner that the final pressure has reached about 30 mmHg.

When the reaction mixture is dissolved in chloroform and subjected to a thin layer chromatography on silica gel (developer : chloroform), it is separated to two parts, one being a component containing no nitrogen, the other being a component containing nitrogen and phosphor.

According to elementary analysis, the latter component is a single compound of Formula I wherein an atomic ratio of nitrogen to phosphor is 1 : 1, $x$ is 2 and $y$ is 4. This compound is used for an identification material in later Examples.

EXAMPLE 2

In the same procedure as Example 1, a single compound of Formula I wherein Z is phenyl and $y$ is 4 is obtained using 800 g of 10-hydroxymethyl-HCA and 50 g of benzoguanamine. This compound is used for an identification material in later Examples.

EXAMPLE 3

50 g of 10-hydroxymethyl-HCA, 150 g of melamine and dimethylformamide are charged into the same flask as in Example 1 and heated to boiling temperature of the contents. At this time the resulting water is distilled out together with a small amount of dimethylformamide. After 4 hours reaction, the reaction mixture is separated by a thin layer chromatography in the same manner as in Example 1.

Thus, a single compound of Formula I wherein Z is $NH_2$-, $x$ is 0 and $y$ is 1 is obtained.

According to elementary analysis, a atomic ratio of N to P is 6 : 1. This compound is used for an identification material in later Examples.

EXAMPLE 4

Using 40 g of 10-hydroxymethyl-HCA, 170 g of benzoguanamine and dimethylformamide, a single compound of Formula I wherein Z = phenyl and $y = 1$ is obtained in the same procedure as in Example 3. The atomic ratio of N to P is 5 : 1.

EXAMPLE 5

6000 g of 10-hydroxymethyl-HCA and 560 g of melamine are charged into a three-necked, 10000 ml flask and elevated to 170° C and then, stirring is effected. The contents are further elevated to 230° C and maintained at same temperature for one hour, during the period of which water is drained out. Next, the inside of the flask is put under vacuum to remove water. The contents are maintained at 230° C for 3 hours in such a manner that the final pressure has reached about 30 mmHg.

When the reaction products are poured into a stainless vat at this temperature and then cooled, an amber glassy solid having a softening point of 157° C is obtained.

According to the infrared absorption spectrum of this product, the absorption at wave number 3170 based on hydroxyl radical of the starting compound disappears and the absorption at wave number 3390 based on the N — H bond is reduced. It is clear from this fact that a dehydration condensation is effected between the hydroxyl radical and the amino radical.

The presence of a main product of Formula I wherein $x = 2$ and $y = 4$ is confirmed by liquid chromatography using the single compound obtained in Example 1 as an identification material.

EXAMPLE 6

6000 g of 10-hydroxymethyl-HCA and 1730 g of benzoguanamine are charged into the same flask as in Example 5, elevated to 170° C and then, stirred.

After elevating to 210° C, the inside of the flask is put under vacuum and a dehydration reaction is effected for 4 hours. The reaction is completed in such a manner that the final pressure has reached about 30 mmHg. After cooling, a light yellow glassy solid having a softening point of 125° C is obtained.

The infrared absorption spectrum of this product is the same as that of Example 5 and shows that a dehydration reaction is effected between the hydroxyl radical of the starting organophosphorus compound and the N — H bond of benzoguanamine.

The presence of a compound of Formula I wherein Z = phenyl and $y = 4$ is confirmed by liquid chromatography using the identification material of Example 2.

EXAMPLE 7

A dehydration reaction is effected in the same procedure as in Example 6 except that 6000 g of 10-hydroxymethyl-HCA and 1025 g of melamine are used.

After cooling, the reaction products have the same appearance as that of Example 5 and a softening point of 153° C.

The presence of a product of Formula I wherein $x = 0$ and $y = 1$ is confirmed by liquid chromatography using the identification material of Example 3.

EXAMPLE 8

6000 g of 6,8-dichloro-10-hydroxymethyl-9,10-dihydro-9-oxa-10-phosphorphenanthrene-10-oxide and 800 g of melamine are charged into the same flask as in Example 5, elevated to 190° C and stirred. After elevating to 230° C, the inside of the flask is put under vacuum. After 4 hours, a dehydration reaction is completed in such a way that the final pressure has reached about 30 mmHg.

The reaction product obtained is a yellow glassy solid having a softening point of 130° C. The infrared absorption spectrum shows that the absorption at wave number 3170 based on hydroxyl radical of the starting compound disappears and the absorption at wave number 3390 based on the N — H bond of melamine is reduced and thus, the reaction is completed.

According to liquid chromatography, the reaction product is a chlorine-substituted compound having the same structure as that of the product obtained in Example 7.

EXAMPLE 9

The procedure of Example 7 is repeated using 6000 g of 2,6,8-tri-tert.-butyl-10-hydroxymethyl-9, 10-dihydro-9-oxa-10-phosphorphenanthrene-10-oxide and 600 g of melamine.

A light yellow, glassy solid having a softening point of 105° C is obtained. According to the infrared absorption spectrum and liquid chromatography, the reaction product is a tert.-butyl-substituted compound having the same structure as that of the product of Example 7.

EXAMPLE 10

The procedure of Example 7 is repeated using 6000 g of 2-methyl-6-tert.butyl-8-methyl-10-hydroxymethyl-9, 10-dihydro-9-oxa-10-phosphorphenanthrene-10-oxide and 700 g of melamine.

A light yellow, glassy solid having a softening point of 115° C is obtained. According to the infrared absorption spectrum and liquid chromatography, the reaction product is a $CH_3$- and t-Bu- substituted compound having the same structure as that of the product of Example 7.

EXAMPLE 11

The same procedure as Example 8 is effected using 6000 g of 8-phenyl-10-hydroxymethyl-9, 10-dihydro-9-oxa-10-phosphorphenanthrene-10-oxide and 800 g of melamine. A light yellow, glassy solid having a softening point of 170° C is obtained. According to the infrared absorption spectrum and liquid chromatography, the reaction product is a phenyl-substituted compound having the same structure as that of the product of Example 7.

EXAMPLE 12

561 g (3.0 mols) of benzoguanamine, 225 g (3.0 × 2 mols) of a 80% paraform and 962 g (3.0 × 5 mols) of butanol are fed into a four-necked flask of 2000 ml in capacity provided with a stirrer, a thermometer, a gas inlet and a dehydration apparatus equipped with a packed column type rectifier of 3 cm in diameter and 40 cm in filler height and a reflux condenser.

Nitrogen gas is slowly blown in while stirring the contents of the flask, and the temperature of the contents is elevated to 80° C.

When the reaction mixture is rendered alkaline by adding 2.0 ml of a 10% aqueous solution of sodium carbonate, addition of formaldehyde to benzoguanamine takes place and after about one hour, the inside of the flask becomes transparent.

After maintaining the temperature at 80° C for a further one hour, 0.5 ml of formic acid are added and this temperature is maintained for one hour. Thereafter 100 ml of benzene are poured slowly into the reaction mixture from the top of the dehydration apparatus.

Then, the contents of the flask are boiled in such a manner that flooding does not take place in the packed column, and water is removed by an azeotropic method. Benzene and butanol are removed from the dehydration apparatus, and the temperature of the contents is elevated to 120° C. After cooling, insoluble materials are filtrated out and thus, dibutoxymethyl benzoguanamine is obtained.

1,296 g (3.0 × 2 mols) of HCA are charged into a four-necked flask of 2,000 ml in capacity provided with a stirrer, a thermometer, a dropping funnel and a vacuum distiller equipped with a rectifying column of 4 cm in diameter and 20 cm in a filler height.

After elevating the temperature of the contents to 130° C, stirring is started and the inside of the flask is put under vacuum of 30 mmHg.

Then, the entirety of the above dibutoxymethyl benzoguanamine is dropped from the dropping funnel. The dropping rate is controlled in such a manner that reflux from the top of the rectifying column is effected slightly so as not to start flooding.

At this time, heating is continued and the temperature is maintained at 130° C. After dropping, the inside of the flask is put under vacuum of about 5 mmHg and elevated slowly to 200° C. After about 6 hours at 200° C, the reaction is completed. Then, the reaction products are poured over a stainless vat and cooled.

The end of reaction is determined by confirming the disappearance of HCA by means of liquid chromatography.

The products thus obtained are a light yellow, transparent, glassy solid, having a softening point of 125° - 142° C according to a capillary tube method. According to a infrared absorption spectrum, an absorption peak at wave number 2,370 based on the stretching vibration of the P — H bond of the starting material and two sharp absorption peaks at wave number of about 3,400, based on the stretching vibration of the N — H bond disappear, and one broad, weak absorption peak at wave number 3,350 based on the stretching vibration of the intramolecular hydrogen bond N — H is observed.

The main product is isolated by a column chromatography on silica gel and subjected to an elementary analysis.

Calculated : P 9.64; N 10.89; C 16.80; H 4.20% Found : P 9.61; N 11.0; C 16.80; H 4.09%.

Molecular Weight (measured by an ebullioscopic method): 625

From these data it is confirmed that the main product has the structure of Formula VIII.

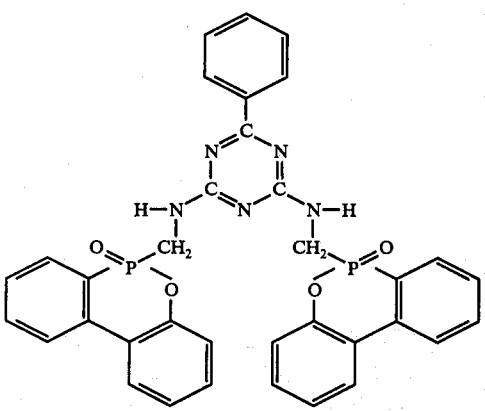

VIII

According to the liquid chromatography, it is also confirmed that the reaction products have the compound of Formula VIII of 82% by weight.

EXAMPLE 13

In the same procedure as in Example 12, butoxymethyl benzoguanamine is obtained from 561 g (3.0 mols) of benzoguanamine, 124 g (3.0 × 1.1 mols) of a 80% paraform and 962 g (3.0 × 5 mols) of butanol. 713 g (3.0 × 1.1 mols) of HCA are charged and the entirety of the above butoxymethyl benzoguanamine is dropped at 130° C in the same manner as in Example 12. After dropping, the inside of the flask is put under vacuum of about 5 mmHg and elevated to 210° C. After 2 hours at the same temperature, the reaction products are poured into a stainless vat and cooled.

The product is a light yellow, transparent, glassy solid, having a softening point of 115° - 132° C. According to liquid chromatography detecting the ultraviolet absorption at wave number 254 m$\mu$, the reaction product indicates about 39% of the compound of Formula VIII, about 17% of benzoguanamine and 42% of the largest peak in respect of peak area. A single compound corresponding to this largest peak is isolated by a thin layer chromatography and subject to elementary analysis. The atomic ratio of N to P is 5 : 1. It is clear from the foregoing that the main product of this Example is a compound of Formula I wherein Z is phenyl, $y$ is 1, and $R_1$, $R_2$ and $R_3$ each is hydrogen.

EXAMPLE 14

252 g of melamine, 515 g (2.0 × 3 mols) of a 35% formalin and 2 ml of a 10% aqueous solution of sodium carbonate are charged into the same flask as in Example 12. Nitrogen gas is slowly blown in while stirring the contents of the flask and the temperature of the contents is elevated to 65° C.

After about 30 minutes the contents become transparent. Then, butanol is added dropwise so as not to make the contents opaque and after one hour, butanol is further added till the whole amount of butanol has reached 962 g (2.0 × 7.5 mols).

The flask is heated and about 300 g of water are removed by subjecting water and butanol to azeotropy.

At this time, 0.5 ml of formic acid from the top of the rectifying column and 100 ml of benzene from the top of the reflux condenser are added.

After 15 hours azeotropy, water is hardly distilled out and then, benzene and butanol are removed till the temperature of the contents has reached 118° C. After cooling, insoluble materials are filtrated out and thus, tributoxymethyl melamine is obtained.

Next, 1,296 g (2.0 × 3 mols) of HCA are charged into the same flask as in Example 12 and elevated to 140° C, and the inside of the flask is put under vacuum of 17 mmHg. While stirring the contents of the flask, the entirety of the above tributoxymethyl melamine is dropped in the same manner as in Example 12.

During the dropping, temperature is slowly elevated in such a way that the temperature after dropping has reached 190° C. After completing the dropping, the contents are further elevated to a temperature of 215° C and after 1.5 hours, the reaction is completed.

The contents are poured into a stainless vat at this temperature and cooled.

The products thus obtained are a colorless transparent, glassy solid, having a softening point of 145° - 163° C. According to the infrared absorption spectrum, a broad, weak absorption based on the intramolecular hydrogen bond N — H is observed at wave number 3,350.

The main product is isolated by column chromatography in the same manner as in Example 12 and subjected to elementary analysis and measurement of molecular weight.

Molecular weight: 852
P content: 11.25%
N content: 9.98%

From these data it is confirmed that the main product of this Example has the following formula IX.

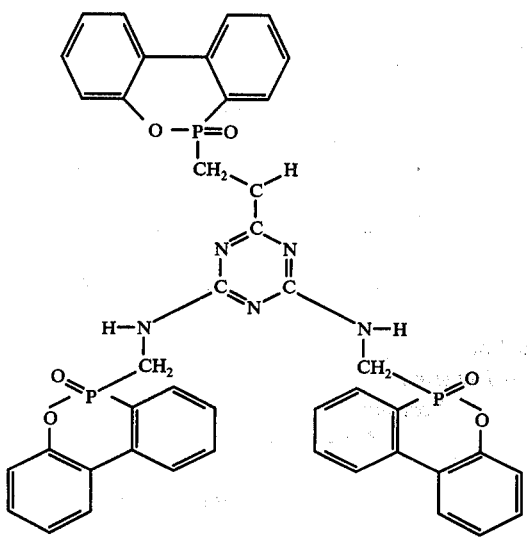

IX

EXAMPLE 15

374 g (2.0 mols) of benzoguanamine, 127 g (2.0 × 2 mols) of a 95% paraform, 1,280 g (2.0 × 20 mols) of methanol and 0.1 g of sodium hydroxide are charged into a four-necked flask of 2,000 ml in capacity provided with a stirrer, a thermometer, a gass inlet and a reflux condenser. Nitrogen gas is slowly blown in while stirring the contents of the flask. When the temperature of the contents is elevated to 60° C, the contents become transparent. After one hour, 1.0 ml of formic acid is added and the contents is heated to such a degree that reflux is slowly effected, for 10 hours.

After cooling, insoluble materials are filtered out and thus, dimethoxymethyl benzoguanamine is obtained.

Next, 1,140 g (2.0 × 2 mols) of 6,8-dichloro-9, 10-dihydro-9-oxa-10-phosphorphenanthrene-10-oxide are charged into a four-necked flask of 2,000 ml in capacity provided with a stirrer, a thermometer, a dropping funnel and a vacuum distillation port equipped with a cold trap which has been cooled by dry ice. The inside of the flask is put under temperature of 170° C and pressure of 3 mmHg. The entirety of the above dimethoxymethyl benzoguanamine is dropped slowly at the same temperature. At this time, volatile materials are almost all removed from the reaction mixture, which are then condensed in the cold trap.

After completion of the dropping, the reaction mixture is elevated to temperature of 200° C and maintained at this temperature for 5 hours thereby to complete the reaction. The reaction products are poured into a stainless vat at the same temperature and cooled. Thus, a light yellow, transparent glassy solid is obtained. Softening Point: 105° - 126° C.

According to infrared absorption spectrum, liquid chromatography, elementary analysis and measurement of molecular weight, it is confirmed that the main product corresponds to a chlorine-substituted product of the compound of Formula VIII and amounts to 76% by weight of the reaction products.

Molecular weight: 782, Cl: 18.5%, P 7.95%, N 9.0%.

EXAMPLE 16

1,296 g (3.0 × 2 mols) of HCA are charged into a four-necked flask of 2,000 ml in capacity provided with a stirrer, a thermometer, a dropping funnel and a vacuum distiller equipped with a rectifying column of 4 cm in diameter and 20 cm in a filler height. The inside of flask is put under temperature of 130° C and pressure of 30 mmHg.

Next, a solution of dibutoxymethyl melamine in butanol which has been obtained starting from 3.0 mols of melamine and 3.0 × 2 mols of formaldehyde in the same procedure as in Example 14 is added while stirring the contents of the flask. After the addition, the contents are elevated slowly to temperature of 200° C and then, the inside of the flask is put under vacuum of 5 mmHg. Heating is further continued and after 6 hours, the contents are poured into a stainless vat and cooled.

The products thus obtained are almost colorless, transparent glassy solid.

Softening Point: 135° - 150° C.

According to liquid chromatography, the reaction products have about 35 wt.% of melamine tri-substituted by the phosphor compound (i,e. compound of Formula IX; $x=1$, $y=2$), about 40 wt.% of the di-substituted melamine (i,e. $x=0$, $y=2$), and about 17 wt.% of the mono-substituted melamine (i,e. $x=0$, $y=1$).

EXAMPLE 17

In the same procedure as Example 12, a condensation reaction is effected under the condition of 18 mmHg, 235° C and 1.5 hours, using 1,168 g (2.0 × 2 mols) of 8-phenyl-9, 10-dihydro-9-oxa-10-phosphor-phenanthrene-10-oxide and 2 mols of dibutoxymethyl benzoguanamine.

A yellow glassy solid having a softening point of 145° - 160° C is obtained. According to the liquid chromatography and elementary analysis, it is confirmed that the main product corresponds to a compound of Formula I wherein $R_1$ is phenyl, $R_2$ and $R_3$ each is hydrogen, Z is phenyl and $y$ is 2.

Molecular weight: 800. P 7.80%; N 8.8%

EXAMPLE 18

This example is to show that compounds of this invention impart a remarkable flame retardancy to synthetic resins. Rating of a flame retardancy is decided by measuring a burning time of a test sample according to the standard of Underwriter's Laboratories Inc., Subject 94 (hereinafter referred to as a method of UL-94). The sample is 3.2 mm thickness, 12.2 mm wide and 152.4 mm long.

5 parts by weight of the product having a softening point of 157° C, obtained in Example 5 are added to 100 parts by weight of polyethylene terephthalate having a number average molecular weight of 27,000, and blended in Brabender mill for 10 minutes. A sample for a burning test according to the method of UL-94 is obtained by subjecting the compounds to compression molding under the condition of 290°, 200 Kg/cm² and 5 minutes.

As a result of the burning test, the maximum burning time is 9.1 seconds and the average is 4.1 seconds and thus, this sample is rated V-O.

The same tests are effected using the organic phosphor compound in an amount as set forth in Table 1. For comparison, an example not using the organic phosphorus compound is set forth in Table 1.

Table 1

| Organic Phosphorus Compounds | Amounts[*] | Burning Test | | |
|---|---|---|---|---|
| | | Maximum, second | Average, second | Rating |
| Products of Example 5 | 2.0 | 22.8 | 14.8 | V-1 |
| Products of Example 6 | 5.0 | 8.5 | 5.2 | V-1 |
| Products of Example 6 | 2.0 | 18.0 | 11.5 | V-1 |
| Non | — | Entirely burnt | — | SB |

[*]Parts by weight per 100 parts by weight of polyethylene terephthalate.

EXAMPLE 19

100 parts by weight of resol type phenolic resin powders and 4 parts by weight of the product of Example 7, having a softening point of 153° C are compounded in Brabender mill at 120° C for 10 minutes. A test sample for the method of UL-94 is obtained by subjecting the compounds to compression molding under the condition of 160° - 170° C, 100 Kg/cm² and 5 minutes.

As a result of the burning test, the maximum burning time is 8.4 seconds and the average 4.6 seconds and thus, this sample is rated V-O.

Moldings of a resin not containing the organic phosphorus compound are entirely burnt and rated SB.

When an amount of the organic phosphorus compounds is reduced to 2.0 parts by weight, the maximum burning time is 28.5 seconds and the average is 18.4 seconds.

100 parts by weight of a curing type melamine prepolymer in the ratio of formalin to melamine of 3.5:1 and 4 parts by weight of the reaction product of Example 7 are blended at 100° C for 5 minutes, and subject to compression molding under the condition of 155° C, 150 Kg/cm² and 2 minutes.

The sample thus obtained is used for the burning test. The maximum burning time is 5.5 seconds and the average is 2.5 seconds and thus, this sample is rated V-O. When an amount of the organic phosphorus compound is reduced to 2.0 parts by weight, the maximum burning time is 19.5 seconds and the average is 12.0 seconds.

What is claimed is:

1. Phosphorus-containing condensation products having the structure represented by the following Formula I, $$\left( \begin{array}{c} Z \\ | \\ C \\ N \diagup \diagdown N \\ \| \quad \| \\ C \quad C \\ \diagdown N \diagup \diagdown N \diagup \end{array} \right) H_{4-y}X_y \quad I$$

wherein Z represents radical $\bigcirc$ or $-NH_{2-x}X_x$ and X is radical $$\begin{array}{c} R_2 \\ R_3 \diagup \diagdown \diagup \diagdown \\ | \quad | \\ O=P \diagup \diagdown O \quad R_1 \\ | \\ CH_2- \end{array} \quad II$$

wherein $R_1$, $R_2$ and $R_3$ each is hydrogen, a halogen atom, an alkyl group of 1 to 8 carbon atoms, an aralkyl group, cyclohexyl or phenyl, $x$ is 0, 1 or 2 and $y$ is from 1 to 4.

2. Phosphorus-containing condensation products of claim 1 wherein Z is phenyl and $y$ is from 1 to 2.

3. Phosphorus-containing condensation products of claim 1 wherein Z is $-NH_{2-x}X_x$, $x$ is 0 or 1 and $y$ is from 1 to 2.

4. Phosphorus-containing condensation products of claim 1 wherein $R_1$, $R_2$ and $R_3$ each is hydrogen.

5. Phosphorus-containing condensation products of claim 1 wherein $R_1$ and $R_2$ each is chlorine and $R_3$ is hydrogen.

6. Phosphorus-containing condensation products of claim 1 wherein $R_1$, $R_2$ and $R_3$ each is tert.-butyl.

7. Phosphorus-containing condensation products of claim 1 wherein $R_1$ is phenyl and $R_2$ and $R_3$ each is hydrogen.

8. Phosphorus-containing condensation products of claim 1 wherein $R_1$ is methyl, $R_2$ is tert-butyl and $R_3$ is hydrogen.

9. A process for the preparation of phosphorus-containing condensation products of Formula I, which comprises conducting a dehydration condensation of organophosphorus compounds represented by Formula III, $$\begin{array}{c} R_2 \\ R_3 \diagup \diagdown \diagup \diagdown \\ | \quad | \\ O=P - O \quad R_1 \\ | \\ CH_2OH \end{array} \quad III$$

wherein $R_1$, $R_2$ and $R_3$ are as defined above with melamine or benzoguanamine.

10. A process for the preparation of phosphorus-containing condensation products of Formula I, which comprises conducting a heating condensation between organophosphorus compounds represented by Formula IV,

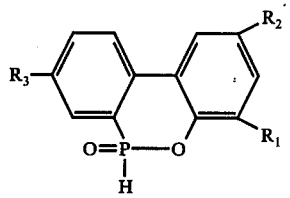

wherein $R_1$, $R_2$ and $R_3$ are as defined above and alkoxymethyl melamines or alkoxymethyl benzoguanamines.

11. A flame retardant resin composition comprising a normally inflammable synthetic resin and a suitable amount of phosphorus-containing condensation products of Formula I

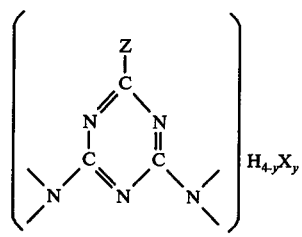

wherein Z represents radical

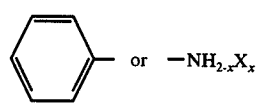

and X is radical

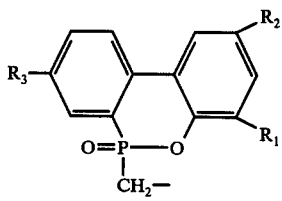

wherein $R_1$, $R_2$ and $R_3$ each is hydrogen, a halogen atom, an alkyl group of 1 to 8 carbon atoms, an aralkyl group, cyclohexyl or phenyl, $x$ is 0, 1 or 2 and $y$ is from 1 to 4.

12. The resin composition of claim 11 wherein the synthetic resin is selected from the group consisting of AS resins, ABS resins, polystyrenes, polycarbonates, polyesters, polyamides, phenoxy resins and aminoplasts.

* * * * *